United States Patent
Eckert et al.

(10) Patent No.: US 11,462,330 B2
(45) Date of Patent: Oct. 4, 2022

(54) SYSTEM AND METHOD FOR PROCESSING WIRELESS BACKSCATTERED SIGNAL USING ARTIFICIAL INTELLIGENCE PROCESSING FOR ACTIVITIES OF DAILY LIFE

(71) Applicant: Koko Home, Inc., Palo Alto, CA (US)

(72) Inventors: Bradley Michael Eckert, Palo Alto, CA (US); Luca Rigazio, Palo Alto, CA (US); Neal Khosla, Palo Alto, CA (US); Kiran Joshi, Palo Alto, CA (US)

(73) Assignee: Koko Home, Inc., Palo Alto, CA (US)

( * ) Notice: Subject to any disclaimer, the term of this patent is extended or adjusted under 35 U.S.C. 154(b) by 0 days.

(21) Appl. No.: 17/526,283

(22) Filed: Nov. 15, 2021

(65) Prior Publication Data

US 2022/0076844 A1 Mar. 10, 2022

Related U.S. Application Data

(63) Continuation of application No. 17/244,554, filed on Apr. 29, 2021, which is a continuation of application (Continued)

(51) Int. Cl.
*G16H 50/30* (2018.01)
*A61B 5/0205* (2006.01)
(Continued)

(52) U.S. Cl.
CPC .......... *G16H 50/30* (2018.01); *A61B 5/0015* (2013.01); *A61B 5/0205* (2013.01);
(Continued)

(58) Field of Classification Search
CPC ...... G16H 50/30; G06N 5/025; A61B 5/0015; A61B 5/0205; A61B 5/7221; A61B 5/746;
(Continued)

(56) References Cited

U.S. PATENT DOCUMENTS

| | | |
|---|---|---|
| 7,436,348 B2 | 10/2008 | Nohmi |
| 7,925,995 B2 | 4/2011 | Krumm et al. |

(Continued)

FOREIGN PATENT DOCUMENTS

| | | |
|---|---|---|
| CN | 207869389 U | 9/2018 |
| GB | 2520169 A | 5/2015 |

(Continued)

OTHER PUBLICATIONS

Wang et al., A Review of Wearable Technologies for Elderly Care That Can Accurately Track Indoor Position, Recognize Physical Activities and Monitor Vital Signs in Real Time, Published: Feb. 10, 2017, Sensors 2017, 36 pp. (Year: 2017).*

(Continued)

*Primary Examiner* — Toan M Le
(74) *Attorney, Agent, or Firm* — Schwegman Lundberg & Woessner, P.A.

(57) ABSTRACT

In an example, the technique also detects and measures vital signs of each human target by continuous, non-intrusive method. In an example, the vital signs of interest include a heart rate and a respiratory rate, which can provide valuable information about the human's wellness. Additionally, the heart rate and respiratory rate can also be used to identify a particular person, if more than two target humans living in a home. Of course, there can be other variations, modifications, and alternatives.

26 Claims, 12 Drawing Sheets

Related U.S. Application Data

No. 16/103,829, filed on Aug. 14, 2018, now Pat. No. 11,004,567.

(60) Provisional application No. 62/545,921, filed on Aug. 15, 2017.

(51) Int. Cl.

| | | |
|---|---|---|
| *A61B 5/00* | (2006.01) | |
| *G06N 5/02* | (2006.01) | |
| *H04B 1/16* | (2006.01) | |
| *H04B 1/04* | (2006.01) | |
| *A61B 5/024* | (2006.01) | |
| *A61B 5/08* | (2006.01) | |
| *A61B 5/11* | (2006.01) | |
| *G16H 40/60* | (2018.01) | |

(52) U.S. Cl.
CPC ........... *A61B 5/7221* (2013.01); *G06N 5/025* (2013.01); *A61B 5/024* (2013.01); *A61B 5/0816* (2013.01); *A61B 5/1113* (2013.01); *A61B 5/1118* (2013.01); *A61B 5/741* (2013.01); *A61B 5/746* (2013.01); *A61B 2503/08* (2013.01); *A61B 2505/07* (2013.01); *A61B 2560/0242* (2013.01); *A61B 2562/0204* (2013.01); *A61B 2562/028* (2013.01); *A61B 2562/029* (2013.01); *A61B 2562/0219* (2013.01); *A61B 2562/0223* (2013.01); *A61B 2562/0228* (2013.01); *A61B 2562/0271* (2013.01); *G16H 40/60* (2018.01); *H04B 1/04* (2013.01); *H04B 1/16* (2013.01)

(58) Field of Classification Search
CPC .... A61B 2560/0219; A61B 2560/0223; A61B 2560/0242; A61B 2562/0219; A61B 2562/0223

See application file for complete search history.

(56) References Cited

U.S. PATENT DOCUMENTS

| | | | |
|---|---|---|---|
| 8,446,253 | B2 | 5/2013 | Ramchandran et al. |
| 9,196,257 | B2 | 11/2015 | Schultz-amling et al. |
| 9,309,782 | B2 | 4/2016 | Kareff et al. |
| 9,319,782 | B1 | 4/2016 | Crump et al. |
| 9,807,725 | B1 | 10/2017 | Vitus et al. |
| 9,972,917 | B2 | 5/2018 | Vacanti et al. |
| 10,568,565 | B1 | 2/2020 | Kahn et al. |
| 10,743,100 | B1 | 8/2020 | Eckert et al. |
| 10,810,850 | B2 | 10/2020 | Eckert et al. |
| 11,004,567 | B2 | 5/2021 | Eckert et al. |
| 11,143,743 | B2 | 10/2021 | Eckert et al. |
| 11,163,052 | B2 | 11/2021 | Eckert et al. |
| 11,175,393 | B2 | 11/2021 | Eckert et al. |
| 11,184,738 | B1 | 11/2021 | Rigazio et al. |
| 11,218,800 | B2 | 1/2022 | Eckert et al. |
| 2005/0154929 | A1 | 7/2005 | Ahrens et al. |
| 2006/0053110 | A1 | 3/2006 | Mcdonald et al. |
| 2006/0152404 | A1 | 7/2006 | Fullerton et al. |
| 2006/0284791 | A1 | 12/2006 | Chen et al. |
| 2007/0205937 | A1 | 9/2007 | Thompson et al. |
| 2007/0297695 | A1 | 12/2007 | Aratani et al. |
| 2009/0167862 | A1 | 7/2009 | Jentoft et al. |
| 2009/0224963 | A1 | 9/2009 | Nakanishi |
| 2010/0026479 | A1 | 2/2010 | Tran |
| 2010/0048256 | A1 | 2/2010 | Huppi et al. |
| 2010/0141506 | A1 | 6/2010 | Gulden et al. |
| 2010/0321229 | A1 | 12/2010 | Dwelly et al. |
| 2011/0077758 | A1 | 3/2011 | Tran et al. |
| 2011/0187816 | A1 | 8/2011 | Shimizu |
| 2011/0190594 | A1 | 8/2011 | Heit et al. |
| 2011/0242305 | A1 | 10/2011 | Peterson et al. |
| 2012/0065944 | A1 | 3/2012 | Nielsen et al. |
| 2012/0275236 | A1 | 11/2012 | Hess et al. |
| 2013/0053653 | A1 | 2/2013 | Cuddihy et al. |
| 2014/0022940 | A1 | 1/2014 | Apte et al. |
| 2014/0207292 | A1 | 7/2014 | Ramagem et al. |
| 2014/0316261 | A1 | 10/2014 | Lux et al. |
| 2014/0375521 | A1 | 12/2014 | Andujar Linares et al. |
| 2015/0079809 | A1 | 3/2015 | Silva et al. |
| 2015/0233598 | A1 | 8/2015 | Shikii et al. |
| 2015/0245167 | A1 | 8/2015 | Bobrow et al. |
| 2015/0265922 | A1 | 9/2015 | Yamane et al. |
| 2015/0286948 | A1 | 10/2015 | Luca et al. |
| 2015/0301167 | A1 | 10/2015 | Sentelle et al. |
| 2015/0310726 | A1 | 10/2015 | Sager et al. |
| 2016/0055332 | A1 | 2/2016 | Jeansonne et al. |
| 2016/0249021 | A1 | 8/2016 | Mcaleenan et al. |
| 2016/0337441 | A1 | 11/2016 | Bloomquist et al. |
| 2016/0377705 | A1 | 12/2016 | Zack et al. |
| 2017/0038456 | A1 | 2/2017 | Smith |
| 2017/0108581 | A1 | 4/2017 | Morley |
| 2017/0328995 | A1 | 11/2017 | Marschalkowski et al. |
| 2018/0031374 | A1 | 2/2018 | Hepler et al. |
| 2018/0050800 | A1 | 2/2018 | Boykin et al. |
| 2018/0143320 | A1 | 5/2018 | Steever et al. |
| 2018/0295535 | A1 | 10/2018 | Kavars et al. |
| 2018/0351775 | A1 | 12/2018 | Zhang et al. |
| 2018/0357871 | A1 | 12/2018 | Siminoff |
| 2019/0033440 | A1 | 1/2019 | Boolos et al. |
| 2019/0043466 | A1 | 2/2019 | Masterson et al. |
| 2019/0057777 | A1 | 2/2019 | Joshi et al. |
| 2019/0072669 | A1 | 3/2019 | Duque Biarge et al. |
| 2019/0088098 | A1 | 3/2019 | Gangumalla et al. |
| 2019/0158494 | A1 | 5/2019 | Nakayama et al. |
| 2019/0197866 | A1 | 6/2019 | Mukundala et al. |
| 2019/0207850 | A1 | 7/2019 | Kearney et al. |
| 2019/0219403 | A1 | 7/2019 | Hu |
| 2019/0278555 | A1 | 9/2019 | Carvajal et al. |
| 2019/0347925 | A1 | 11/2019 | Faltaous et al. |
| 2019/0372363 | A1 | 12/2019 | Cutcher et al. |
| 2019/0375103 | A1 | 12/2019 | Cui et al. |
| 2020/0053574 | A1 | 2/2020 | Hasan et al. |
| 2020/0054236 | A1 | 2/2020 | Qi et al. |
| 2020/0079363 | A1 | 3/2020 | Frederick et al. |
| 2020/0097092 | A1 | 3/2020 | Tzadok |
| 2020/0103486 | A1 | 4/2020 | Knaappila |
| 2020/0103513 | A1 | 4/2020 | Knaappila |
| 2020/0143123 | A1 | 5/2020 | Shen et al. |
| 2020/0158819 | A1 | 5/2020 | Joshi et al. |
| 2020/0158849 | A1 | 5/2020 | Joshi et al. |
| 2020/0196110 | A1 | 6/2020 | Jakobsson |
| 2020/0204541 | A1 | 6/2020 | Nair et al. |
| 2020/0234030 | A1 | 7/2020 | Baheti et al. |
| 2020/0256972 | A1 | 8/2020 | Eckert et al. |
| 2020/0260180 | A1 | 8/2020 | Eckert et al. |
| 2020/0264278 | A1 | 8/2020 | Eckert et al. |
| 2020/0265698 | A1 | 8/2020 | Eckert et al. |
| 2020/0271747 | A1 | 8/2020 | Wu et al. |
| 2020/0272268 | A1 | 8/2020 | Shin et al. |
| 2020/0310749 | A1 | 10/2020 | Miller et al. |
| 2020/0039731 | A1 | 12/2020 | Gu et al. |
| 2021/0033724 | A1 | 2/2021 | Zhang et al. |
| 2021/0035425 | A1 | 2/2021 | Eckert et al. |
| 2021/0037315 | A1 | 2/2021 | Eckert et al. |
| 2021/0065891 | A1 | 3/2021 | Li et al. |
| 2021/0096216 | A1 | 4/2021 | Rigazio et al. |
| 2021/0150873 | A1 | 5/2021 | Shouldice et al. |
| 2021/0197834 | A1 | 7/2021 | Shaker et al. |
| 2021/0249140 | A1 | 8/2021 | Eckert et al. |
| 2021/0360344 | A1 | 11/2021 | Eckert et al. |
| 2021/0377657 | A1 | 12/2021 | Cnaan et al. |
| 2022/0091248 | A1 | 3/2022 | Eckert et al. |
| 2022/0182791 | A1 | 6/2022 | Eckert et al. |

FOREIGN PATENT DOCUMENTS

| | | | |
|---|---|---|---|
| KR | | 101536249 B1 | 7/2015 |

(56) References Cited

FOREIGN PATENT DOCUMENTS

WO  WO-2016193972 A2  12/2016
WO  WO-2020102813 A1  5/2020

OTHER PUBLICATIONS

Rahman et al., DoppleSleep: A Contactless Unobtrusive Sleep Sensing System Using Short-Range Doppler Radar, Sep. 7-11, 2015, UBICOMP '15, Osaka, Japan, pp. 39-50 (Year: 2015).*
"U.S. Appl. No. 16/103,829, Non Final Office Action dated Jul. 13, 2020", 13 pgs.
"U.S. Appl. No. 16/103,829, Notice of Allowance dated Jan. 14, 2021", 11 pgs.
"U.S. Appl. No. 16/103,829, Response filed Dec. 8, 2020 to Non Final Office Action dated Jul. 13, 2020", 11 pgs.
"International Application Serial No. PCT/US2019/062043, International Search Report dated Mar. 19, 2020", 3 pgs.
Yang, et al., "Vital Sign and Sleep Monitoring Using Millimeter Wave", ACM Transactions on Sensor Networks, vol. 13, No. 2, Artical 14, (Apr. 2017), 32 pgs.
"U.S. Appl. No. 16/279,949, Non Final Office Action dated Apr. 13, 2022", 17 pgs.
"U.S. Appl. No. 17/074,053, Examiner Interview Summary dated Mar. 8, 2022", 2 pgs.
"U.S. Appl. No. 17/074,053, Final Office Action dated Apr. 4, 2022", 19 pgs.
"U.S. Appl. No. 17/074,053, Response filed Mar. 9, 2022 to Non Final Office Action dated Feb. 24, 2022", 9 pgs.
Ganis, "A Portable 3D Imaging FMCW MIMO Radar Demonstrator with a 24x24 Antenna Array for Medium Range Applications", (2018), 15 pgs.
Hannun, Awni, et al., "Sequence-tosequence speech recognition with time-depth separable convolutions", arXiv:1904.02619, (Apr. 2019), 5 pgs.
He, Kaiming, et al., "Deep Residual Learning for Image Recognition", arXiv preprint, arXiv:1512.03385v1 [cs.CV], (Dec. 10, 2015), 12 pgs.
Lee, "Design and Performance of a 24-GHz Switch-Antenna Array FMCW Radar System for Automotive Applications", (2010), 8 pgs.
Lien, Jaime, et al., "Soli: Ubiquitous Gesture Sensing with Millimeter Wave Radar", ACM Transactions on Graphics (TOG), vol. 35 Issue 4, Article 142, (Jul. 2016), 19 pgs.
Ravanelli, M, et al., "Speech and Speaker Recognition from Raw Waveform with SincNet", arXiv:1812.05920v2, (Feb. 15, 2019), 5 pgs.
Sherman, "AN/FPS-115 PAVE PAWS Radar", (2000), 4 pgs.
Tian, Yonglong, "RF-Based Fall Monitoring Using Convolutional Neural Networks", Proc. ACM Interact. Mob. Wearable Ubiquitous Technol., vol. 2, No. 3, Article 137, (Sep. 2018), 24 pgs.
Tokoro, S, et al., "Electronically scanned millimeter-wave radar for pre-crash safety and adaptive cruise control system", In IEEE IV2003 Intelligent Vehicles Symposium, (Jun. 2003), 6 pgs.
"U.S. Appl. No. 17/074,053, Examiner Interview Summary dated May 2, 2022", 2 pgs.
"U.S. Appl. No. 17/074,053, Response filed May 6, 2022 to Final Office Action dated Apr. 4, 2022", 9 pgs.
"U.S. Appl. No. 16/588,755, Non Final Office Action dated Jun. 16, 2022", 10 pgs.
"U.S. Appl. No. 17/074,053, Examiner Interview Summary dated Jun. 10, 2022", 2 pgs.
"U.S. Appl. No. 16/279,949, Examiner Interview Summary dated Jul. 15, 2022", 2 pgs.

* cited by examiner

FIGURE 1: Radar\Wireless Backscatter Sensor 100

Figure 2: Full Sensor Array 200

Figure 4: Hardware Units of ADL/Security System

Figure 5: Hub

Figure 7: Mini Node

Figure 9: Mobile Node

Figure 11: Categories of Senior ADL

- Basic ADLs:
    - Bathing
    - Brushing teeth
    - Dressing
    - Using Toilet
    - Eating and Drinking
    - Sleeping
- Instrumented ADLs
    - Preparing meals
    - Preparing drinks
    - Resting
    - Housekeeping
    - Using a telephone
    - Taking medicine
- Ambulatory Activities
    - Walking:
    - Doing Exercise : Running, cycling
    - Transitional Activities : Sit-to-stand, sit-to-lie, stand-to-sit, lie-to-sit in and out of bed or chair
    - Stationary Activities : sits in sofa, stand for a while, lie in bed or sofa

Figure 12: Activities List

- Going Out
- Preparing Breakfast
- Having Breakfast
- Preparing Lunch
- Having Lunch
- Preparing Dinner
- Having Dinner
- Washing Dishes
- Having Snack
- Sleeping
- Watching TV
- Studying
- Having Shower
- Toileting
- Having Nap
- Using Internet
- Reading Book
- Shaving
- Brushing Teeth
- Telephone
- Listening Music
- Doing Cleaning
- Having Conversation
- Entertain Guest

SYSTEM AND METHOD FOR PROCESSING WIRELESS BACKSCATTERED SIGNAL USING ARTIFICIAL INTELLIGENCE PROCESSING FOR ACTIVITIES OF DAILY LIFE

CROSS-REFERENCE TO RELATED APPLICATION

The present application is a continuation of U.S. patent application Ser. No. 17/244,554, filed Apr. 29, 2021 which is a continuation of U.S. patent application Ser. No. 16/103,829 filed Aug. 14, 2018, now U.S. Pat. No. 11,004,567, which is a non-provisional of, and claims the benefit of priority to U.S. Prov. Pat. App. No. 62/545,921 filed Aug. 15, 2017, the entire contents of each is incorporated herein by reference.

BACKGROUND

The present invention relates to techniques, including a method, and system, for processing signals using artificial intelligence techniques to monitor, detect, and act on activities. In an example, the signals can be from both active and passive sensors, among others. Merely by way of examples, various applications can include daily life, and others.

Various conventional techniques exist for monitoring people within a home or building environment. Such techniques include use of cameras to view a person. Other techniques include a pendant or other sensing device that is placed on the person to monitor his/her movement. Examples include Personal Emergency Response Systems (PERS) devices such as LifeAlert® and Philips® LifeLine—each of which are just panic buttons for seniors to press in case of an emergency. Unfortunately, all of these techniques have limitations. That is, each of these techniques fails to provide a reliable and high quality signal to accurately detect a fall or other life activity of the person being monitored. Many people often forget to wear the pendant or a power source for the pendant runs out. Also, elderly people do not want to look like they are old so often times, elderly people do not wear the pendant.

From the above, it is seen that techniques for identifying and monitoring a person is highly desirable.

SUMMARY

According to the present invention, techniques, including a method, and system, for processing signals using artificial intelligence techniques to monitor, detect, and act on activities are provided. In an example, the signals can be from both active and passive sensors, among others. Merely by way of examples, various applications can include daily life, and others.

In an example, the present invention provides a sensor array in a single box that can be placed in a home or a single box (acting as a base station) that talks to multiple helper sensor boxes distributed throughout a living space of the home. In an example, the sensor array will communicate with a backend server via standard connectivity solutions, such as Wi-Fi, cellular, or others. In an example, the technique uses distributed processing where processing of the data occurs inside the sensor array and in a cloud server. In an example, artificial intelligence (AI) techniques are included. Depending upon the example, the processed data are disseminated to various interested parties (e.g., children of elderly person, care takers, Emergency Medical Response team) via different communication channels, such as smartphone app, SMS, email, voicemail, and other techniques.

In an example, the present invention provides a method of detecting a status of a human being or target. The method includes transferring using a wireless transmitter, a wireless signal being selected from one or more of a frequency being less than about 10 G Hz, 24 G Hz, 60 G Hz, or 77 G Hz and greater. The method includes capturing a back scattered signal, using an rf antenna, from the wireless signal. The method includes processing the back scattered signal to extract one or more of a direction, signal strength, distance, and other information over a time period. The method includes extracting, using a signal processing process, vital signs of a human, the vital signs including a heart rate, or a respiration rate. The method includes creating a baseline for each of the vital signs. The method includes extracting, using an AI process, a physical activity of the human being. The method includes creating a physical activity base line for the physical activity and determining a confidence level of each of the received vital signals and each of the physical activities. The method includes transferring an alert to another target upon a triggering even based upon the confidence level of each of the received vital signals and each of the physical activities and correlating each vital sign, using an artificial intelligence process, with one or more patterns or the base line for each of the vital signs.

In an example, the present invention provides a system for monitoring and detecting an activity of a human target. The system has a sensor array, the sensor array comprising a plurality of passive sensors. In an example, each of the plurality of passive sensors is spatially disposed in spatial region of a living area. In an example, the system has a wireless backscattering detection system. The wireless backscattering detection system has a control line coupled to a processing device. In an example, the control line is configured with a switch to trigger an initiation of a wireless signal. The detection system has a waveform pattern generator coupled to the control line, an rf transmitter coupled to the waveform pattern generator, a transmitting antenna coupled to the rf transmitter, an rf receiver, an rf receiving antenna coupled to the rf receiver, an analog front end comprising a filter, an analog to digital converter coupled to the analog front end, a signal processing device coupled to the analog to digital converter, and an artificial intelligence module coupled to the signal processing device, and configured to process information associated with a backscattered signal captured from the rf receiving antenna. Further details of each of these elements can be found throughout the present specification and more particularly below.

The above examples and implementations are not necessarily inclusive or exclusive of each other and may be combined in any manner that is non-conflicting and otherwise possible, whether they be presented in association with a same, or a different, embodiment or example or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above examples implementations are illustrative, rather than limiting.

BRIEF DESCRIPTION OF THE DRAWINGS

FIG. 11 is a simplified diagram illustrating senor ADL categories in an example.

FIG. 12 is a simplified diagram illustrating an activity list according to an example

DETAILED DESCRIPTION OF THE EXAMPLES

According to the present invention, techniques, including a method, and system, for processing signals using artificial intelligence techniques to monitor, detect, and act on activities are provided. In an example, the signals can be from both active and passive sensors, among others. Merely by way of examples, various applications can include daily life, and others.

Figure 1:
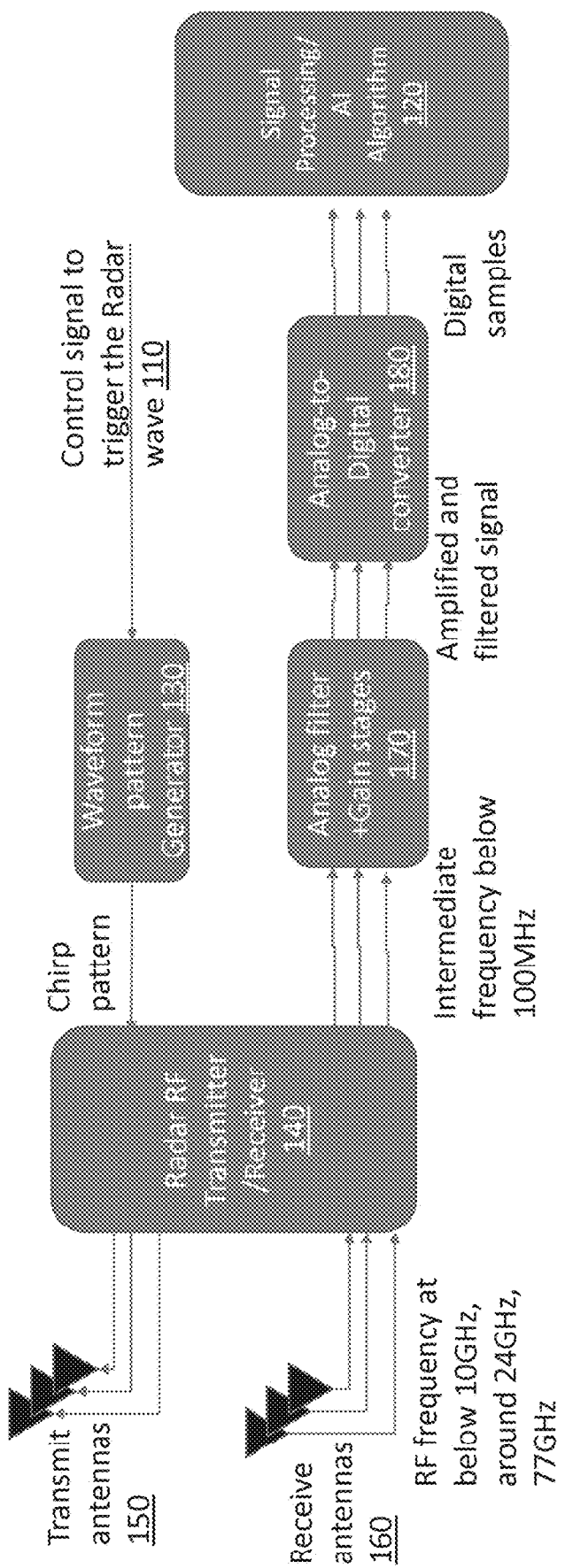
FIG. 1 is a simplified diagram of a radar/wireless backscattering sensor system according to an example of the present invention.

FIG. 1 is a simplified diagram of a radar/wireless backscattering sensor system 100 according to an example of the present invention. This diagram is merely an example, which should not unduly limit the scope of the claims herein. In an example, the system is a wireless backscattering detection system. The system has a control line 110 coupled to a processing device 120, the control line being configured with a switch to trigger an initiation of a wireless signal. In an example, the system has a waveform pattern generator 130 coupled to the control line 110. The system has an rf transmitter 140 coupled to the waveform pattern generator 130. The system has transmitting 150 and receiving 160 antennas. In an example, the system has a transmitting antenna 150 coupled to the rf transmitter 140 and an rf receiver 140, which is coupled to an rf receiving antenna 160. In an example, the system has an analog front end 170 comprising a filter. An analog to digital converter 180 coupled to the analog front end 170. The system has a signal-processing device 120 coupled to the analog to digital converter 180. In a preferred example, the system has an artificial intelligence module coupled to the signal-processing device 120. The module is configured to process information associated with a backscattered signal captured from the rf receiving antenna. Further details of the present system can be found through out the specification and more particularly below.

Antenna

In an example, multiple aspects of antenna design can improve the performance of the activities of daily life ("ADL") system. For example, in scanning mode the present technique continuously looks for moving human targets (or user) to extract ADL or fall. Since these can happen anywhere in the spatial region of a home, the present system has antennas that have wide field of view. Once the human target is identified, the technique focuses signals coming only from that particular target and attenuate returns from all other targets. This can be done by first estimating location of the target from our technique using wide field of view antennas and then focusing RF energy on the specific target of interest once it has been identified. In an example, the technique can either electronically switch a different antenna that has narrow field of view or could use beam forming techniques to simultaneously transmit waves from multiple transmit antenna and control their phase such that the RF energy constructively builds around the target of interest where as it destructively cancels everywhere else. This return will be much cleaner and can boost the performance of our ADL+fall+vital sign sensors.

In another example considers the layout of the antennas itself. In an example, the technique places transmit and receive antennas in various physical configurations (ULA, circular, square, etc.), that can help us establish the direction from which the radar signal returns, by comparing phases of the same radar signal at different receiving antennas. The configurations can play a role because different configurations enable direction of arrival measurement from different dimensions. For example, when the human target falls the vertical angle of arrival changes from top to bottom, therefore a vertical ULA is better suited to capture that information. Likewise during walking horizontal angle of arrival of the signal varies more therefore it makes sense to use horizontal ULA is more sensitive and therefor can provide additional information for our algorithm. Of course, there can be other variations, modifications, and alternatives.

RF Unit

In an example, the wireless RF unit can be either pulsed doppler radar or frequency modulated continuous wave (FMCW) or continuous wave doppler (CW). In an example, on the transmit side it will have standard RF units like VCO, PLL, among others. On the receive side it can have matched filter, LNA, mixer, and other elements. The multiple antennas can be either driven by a single transmit/receive chain by sharing it in time or have one each chain for each of the antennas.

Waveform Unit

In an example, waveform pattern generator generates control signals that define the type of radar signal that is generated by the radar RF unit. For example, for FMCW, it can generate triangular wave of specific slope and period, which will linearly sweep the frequency of the RF unit according to this parameter. For a pulsed doppler radar, the technique will hold generate pulse of specific width and period, which will modulate the RF output accordingly.

Baseband Unit

In an example, the gain and filter stage filters the radar returns to remove any unwanted signals and then amplifies the remaining signal with different techniques. For example, the present artificial intelligence or AI technique can determine what target is desirably tracked and provide feedback to the AI technique, that will filter out radar return from any and all other signals except for the signal that is desirably tracked. If human target is moving the return signal will be fluctuating, in that case, the technique applies automatic gain control (AGC) to find the optimal gain, so that entire dynamic range of ADC in the subsequent stage is satisfied. In an example, the return signal is converted to digital samples by analog-to-digital converters (ADC), among other front-end elements.

Figure 2:
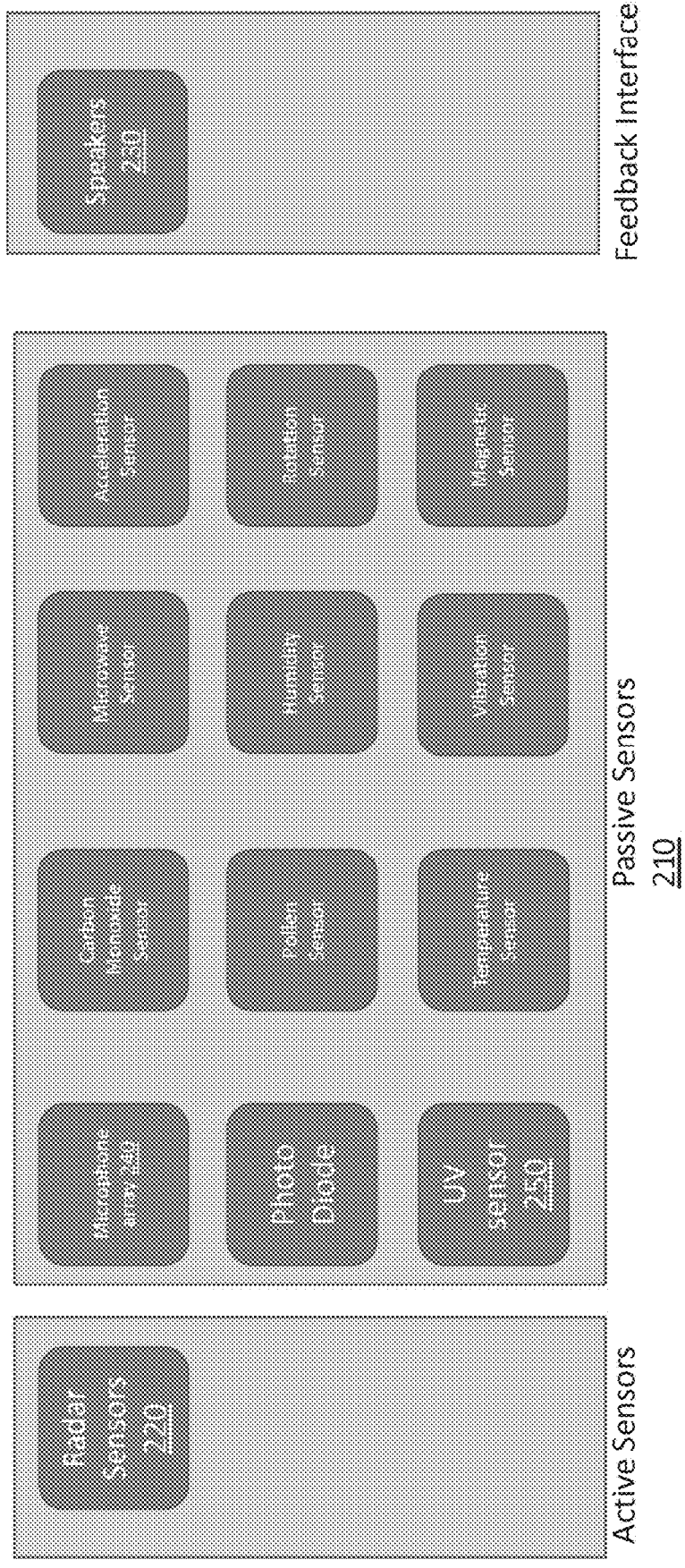
FIG. 2 is a simplified diagram of a sensor array according to an example of the present invention.

FIG. 2 is a simplified diagram of a sensor array 200 according to an example of the present invention. This diagram is merely an example, which should not unduly limit the scope of the claims herein. Shown is a sensor array. The sensor array includes a plurality of passive sensors 210. In an example, the plurality of passive sensors are spatially disposed in spatial region of a living area. The sensor array has active sensors, such as one or more radar sensors 220. Additionally, the array has a feedback interface, such as a speaker 230 for calling out to a human target in the spatial region of the living area.

In an example, the present technique is provided to identify various activities in home using non-wearable. In an example, the technique is at least privacy intrusive as possible, and will use sensors that are less intrusive. Examples of sensors can include, without limitation, a wireless backscatter (e.g., radar, Wi-Fi.), audio (e.g., microphone array, speaker array), video (e.g., PTZ mounted, stereo), pressure mats, infrared, temperature, ultraviolet, humidity, pressure, smoke, any combination thereof, and others.

Active Sensor for RADAR

In an example, the technique can use wireless backscattering to measure motion of human, a location, and an environmental state, such as door opening/closing, or other environmental condition. In an example, the wireless backscattering can also be used to measure a vital sign, such as a heart rate and respiration rate, among others. In an example, the wireless techniques can work in non-line of sight, and is non intrusive compared to camera or microphone, or others. In an example, the technique can use radar\backscatter sensor for two purposes (1) to find the location of an action; and (2) sense different activities associated with the action. Of course, there can be other variations, modifications, and alternatives.

In an example, the present technique and system includes a radar system that operates on multiple frequency bands, such as below 10 GHz, around 24 GHz, 60 GHz, 77-81 GHz, among others. In an example, different frequency interacts differently with various objects in our environment. In an example, available signal bandwidth and permissible signal power are also regulated differently at different frequency bands. In an example, the present techniques optimally combine reflections coming from a reflector from multiple frequency bands to achieve large coverage, and/or improve accuracy. Of course, there can be other variations, modifications, and alternatives.

In an example, each radar is working at a particular frequency band will be using multiple transmit and receive antennas, as shown. In an example, using these multiple transmitters, the technique can perform transmit beam forming to concentrate radar signal on a particular target. In an example, the technique uses multiple receivers to collect reflected signals coming from various reflectors (e.g., human body, walls). After further processing this will allow us to find the direction of the reflector with respect to the radar. In an example, the technique also uses multiple transmitter and receiver to form virtual array, this will allow emulate the radar array with large element by using small number of transmitter and receiver chains. The main benefit is to improve the angle resolution without using a large array, saving space and component cost. In an example, different antenna array configurations to improve coverage (using beam forming) or add 3D localization capability (using 2-D array) are included.

In an example using standard radar signal modulation techniques, such as FMCW/UWB, on MIMO radar, the technique will first separate signals coming from different range and angle. The technique will then identify static reflectors, such as chairs, walls, or other features, from moving ones, such as human targets, pets, or the like. For moving objects that are tracked, the technique will further process signals for each of the reflectors. As an example, the technique will use different techniques to extract raw motion data (e.g., like spectrogram). In an example, the technique will apply various filtering process to extract periodic signals generated by vital signs, such as heart rate, respiration rate, among others. In an example, both the raw motion data and extracted vital signs will be passed to a downstream process, where they are combined with data from other sensors, such as radar outputs operating at different frequency or completely different sensors to extract higher insights about the environment. Of course, there can be other variations, modifications, and alternatives.

Audio Sensor

In an example, the present technique uses a sensor array that has a multiple microphone array 240. In an example, these microphones 240 will be use to ascertain the direction of arrival of any audio signal in the environment. In an example, the microphone 240 in conjunction with other sensors, such as radar 220, will be vital in performing two tasks: 1st it will augment radar signal to identify various activities (walking produces a different sound than sitting), if the target is watching TV it is much easier to ascertain it with audio signal; and 2nd in case of emergency like fall, the technique can use the radar signal to identify the location of the fall and then beam form microphone array towards that location, so that any audio signal produced by the target can be captured. Of course, there can be other variations, modifications, and alternatives.

Sensor Fusion and Soft Sensors

In addition to a radar sensor, which is consider as active sensors the present sensor system (e.g., box, boxes) will also have additional passive sensors that captures the sound, chemical signature, environmental conditions. Each of these of the sensors captures different context about the home that the human being tracking is living in or occupying. In an example, the UV 250 sensor can monitor how often the sunlight comes in the room. In an example, light sensors determine a lighting condition of the human's home or living area.

In an example, a microphone array 240 can have many functions, such as use to sense sound in the room, to figure out how long the human has spent watching TV, or how many time they went to bathroom by listening to the sound of toilet flushing or other audio signature. In an example, the present technique can use creative solutions where it can use the active sensor to find the location of the person and then tune the microphone array to enhance the sound coming from that location only, among other features. In an example, the technique can call the sensors that are derived from the hardware sensors using specific algorithms as software sensors or soft sensors. So the same hardware sensors can be used for many different applications by creating different software sensors. Here the software sensors can combine signals from one or more sensors and then apply sensor fusion and AI techniques to generate the desired output. Of course, there can be other variations, modifications, and alternatives.

Soft Sensor for Detecting Cooking and Eating Habits

In example, radar sensors can determine information about a human's location within a home, like if they are in kitchen area, or other. In an example, when the human target turns on the microphone oven, it generates specific RF signature that can be tracked. In an example, the technique can combine this information to infer if the human target walked to the kitchen and turned on the microphone. Likewise, when the human target prepares food in kitchen he/she can make lot of specific noise like utensils clattering, chopping, or other audio signature. So if a human target goes to kitchen spends sometime time in the kitchen, and the present microphone pick these sounds, the technique can infer that food is cooking or other activity.

Soft Sensor for Detecting Bathroom Habits

In an example, toileting frequency can be a very valuable indication of ones wellness. The present technique can track if a human went to the bathroom using the radar or other sensing techniques. In an example, additionally, the technique can pick sound signature of toilet flushing. In an example, the technique combines these two pieces of information, which can be correlated to toileting frequency. In an example, similarly, bathing is a unique activity that requires 4-5 minutes of specific movements. By learning those patterns, the technique can figure out ones bathing routines.

Soft Sensor for Detecting Mobile Habits

In an example, different sensors are triggered by different motion of a human target. In an example, radar can detect human fall by looking at micro doppler patterns generating by different part of the target during falls. In an example, the technique can also simultaneously hear a fall from microphone arrays and vibration sensors. In an example, the technique can also detect how pace of movement changes for an individual over a long duration by monitoring the location information provided by radar or other sensing technique. In an example, likewise, the technique can gather unstable transfers by analyzing the gait of the target. In an example, the technique can find front door loitering by analyzing the radar signal pattern. In an example, the technique can figure out immobility by analyzing the radar return. In this case, the technique can figure out the target's presence by analyzing the target's vital signs, such as respiration rate or heart rate or by keeping track of the bread crumb of the target's location trace.

In any and all of the above cases, the technique can also learn about the exact environmental condition that triggered a particular state. For example, the technique can figure out whether a human target was immobile because the target was watching TV or a video for long duration or the target was simply spending a lot of time in their bed. And these can be used to devise incentives to change the target's behavioral pattern for better living.

Soft Sensor for Detecting Vital Signs

In an example, the technique can estimate vital signs of a person by sensing the vibration of the target's body in response to the breathing or heart beat, each of the actions results in tiny phase change in the radar return signals, which can be detected. In an example, the technique will use several signal processing techniques to extract them. Of course, there can be other variations, modifications, and alternatives.

In an example, different frequency radio wave interact with environment differently. Also phase change due to vital signs (HR,RR) differs by frequency, for example phase change for a 77 GHz radar is much higher than for a 10 GHz radar. Thus 77 GHz is more appropriate for estimating heart-beat more accurately. But higher frequency typically attenuates much more rapidly with distance. Therefore, lower frequency radar can have much larger range. By using multi-frequency radar in the present technique can perform these vital trade-offs.

Soft Sensor for Detecting Sleeping Habits

In an example, the present radar sensors can detect motions that are generated during sleep, such as tossing and turning. In an example, radar sensors can also sense vital signs like respiration rate and heart rate as described earlier. In an example, now combining the pattern of toss and turn and different breathing and heart beat pattern, the technique can effectively monitor the target's sleep. Additionally, the technique can now combine results from passive sensors, such as a thermometer, UV, photo diode, among others, to find correlation between certain sleep pattern and the environmental conditions. In an example, the technique can also use the sleep monitor soft sensor to learn about day/night reversal of sleep, and the associated environmental condition by looking at different passive sensors. In an example, the techniques can be valuable in providing feedback to improve the human target's sleep. For example, the technique can determine or learn that certain environmental condition results in better sleep and prescribe that to improve future sleep.

Soft Sensor for Security Applications

In an example, the technique can repurpose many of the sensors described before for security applications. For a security application, the technique determines where one or more person is located, which can be detected using a presence detection sensor that is build on top of radar signals. In an example, the technique can eliminate one or many false positive triggered by traditional security systems. For example, is a window is suddenly opened by a wind the technique (and system) will look at presence of human in the vicinity before triggering the alarm. Likewise, combination of vital signs, movement patterns, among others, can be used a biometric to identify any human target. If an unknown human target is detected in the vicinity at certain time of the day, the technique can trigger an alarm or alert.

In an example, any one of the above sensing techniques can be combined, separated, or integrated. In an example, n addition to radar and audio sensors, other sensors can be provided in the sensor array. Of course, there can be other variations, modifications, and alternatives.

Figure 3:
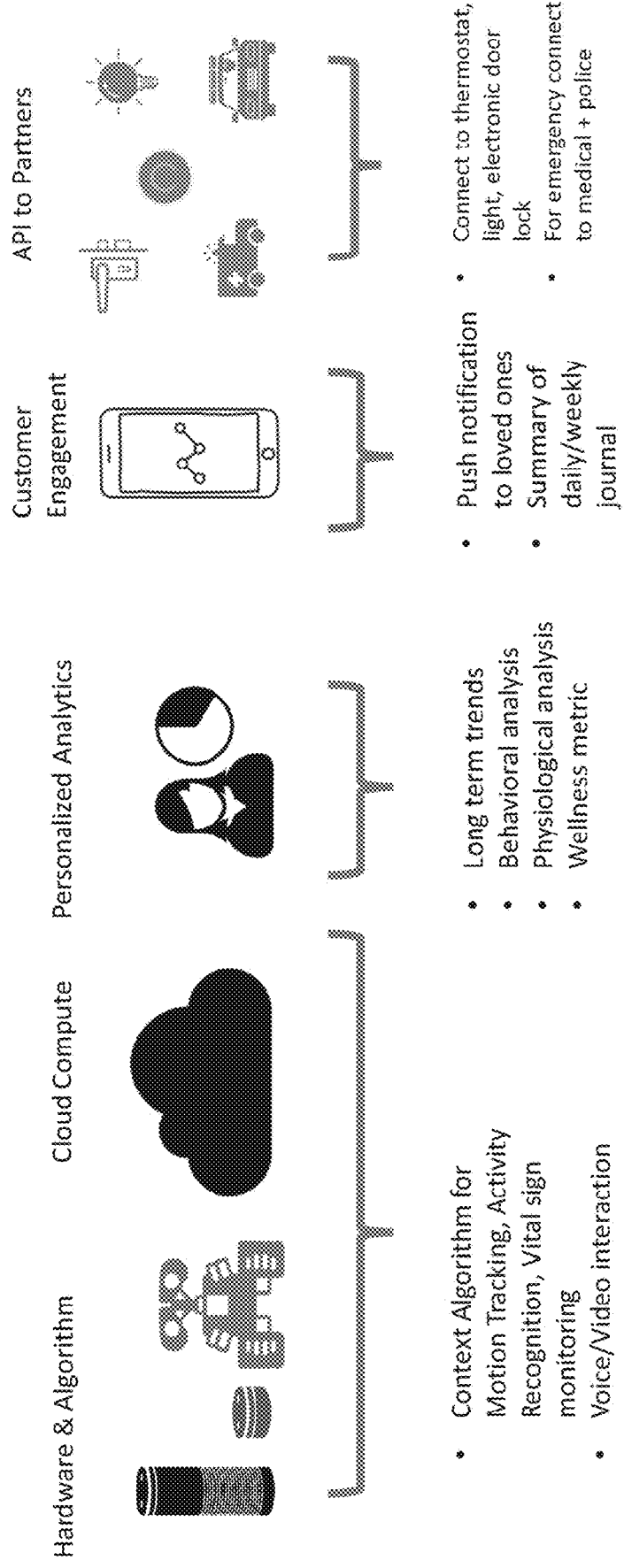
FIG. 3 is a simplified diagram of a system according to an example of the present invention.

FIG. 3 is a simplified diagram of a system according to an example of the present invention. This diagram is merely an example, which should not unduly limit the scope of the claims herein. As shown, the system has hardware and method (e.g., algorithm), cloud computing, personalized analytics, customer engagement, and an API to various partners, such as police, medical, and others. Further details of the present system can be found throughout the present specification and more particularly below.

Figure 4:
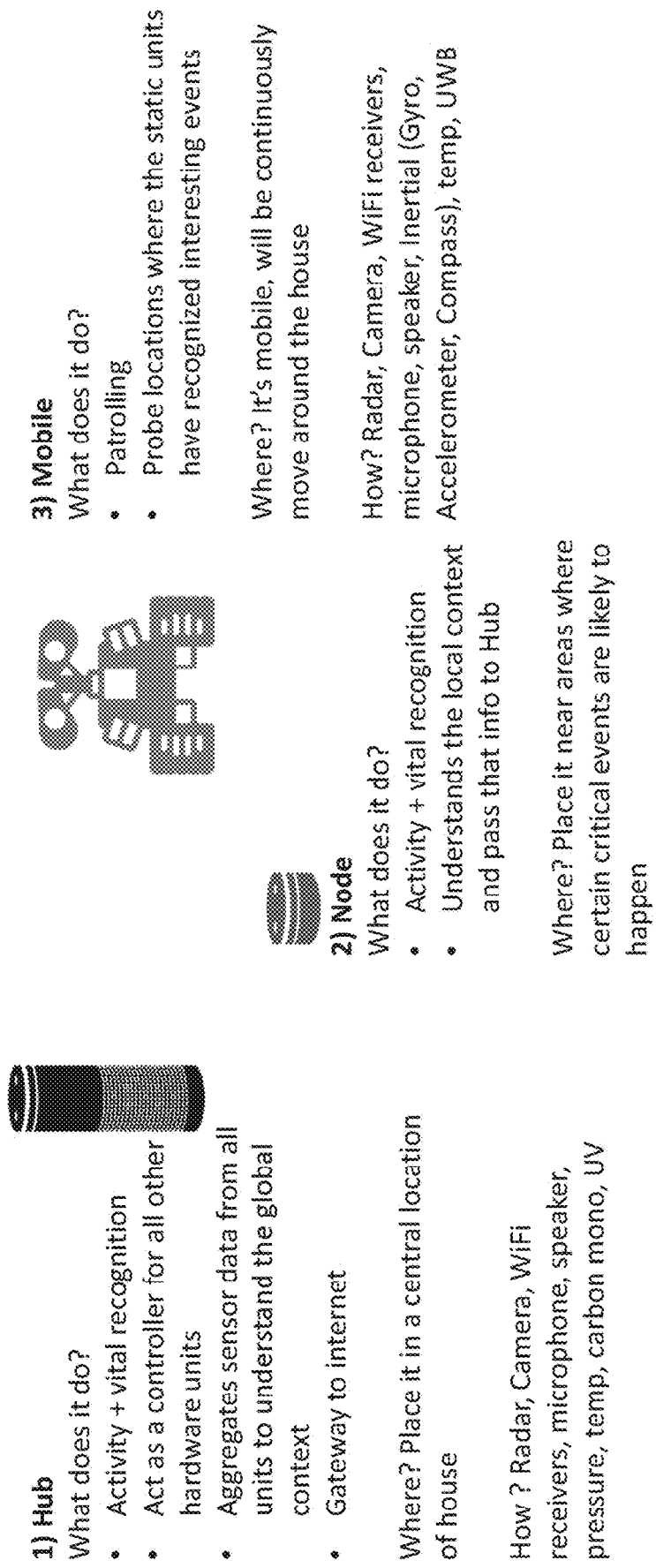
FIG. 4 is a detailed diagram of hardware apparatus according to an example of the present invention.

FIG. 4 is a detailed diagram of hardware apparatus according to an example of the present invention. This diagram is merely an example, which should not unduly limit the scope of the claims herein. As shown, the hardware units include at least a hub device, node, and mobile node, each of which will be described in more detail below.

Figure 5:
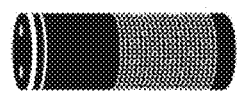
FIG. 5 is a simplified diagram of a hub according to an example of the present invention.

FIG. 5 is a simplified diagram of a hub according to an example of the present invention. This diagram is merely an example, which should not unduly limit the scope of the claims herein. In an example, the hub includes various sensing devices. The sensing devices, include, among others, a radar, a WiFi, a Bluetooth, a Zigbee sniffer, a microphone and speakers, a smoke detector, a temperature detector, a humidity detector, a UV detector, a pressure detector, MEMS (e.g., accelerometer, gyroscope, and compass), a UWB sensors (for finding locations of all the deployed elements relative to each other), among others. In an example, the hub is a gateway to internet via Wi-Fi, GSM, Ethernet, landline, or other technique. The hub also connects to other units (Mini Node/Mobile Node) via Bluetooth, Wi-Fi, Zigbee, UWB and coordinates them with each other. In an example, certain data processing, such as noise removal, feature extraction to reduce amount of data uploaded to cloud is included. In an example, the hub alone can be sufficient to cover a small living space. In an example, the hub is deployed as a single device somewhere in a desirable location (e.g., middle of the living space) so that it has good connectivity to all other units. An example of such deployment is provided in the Figure below.

Figure 6:
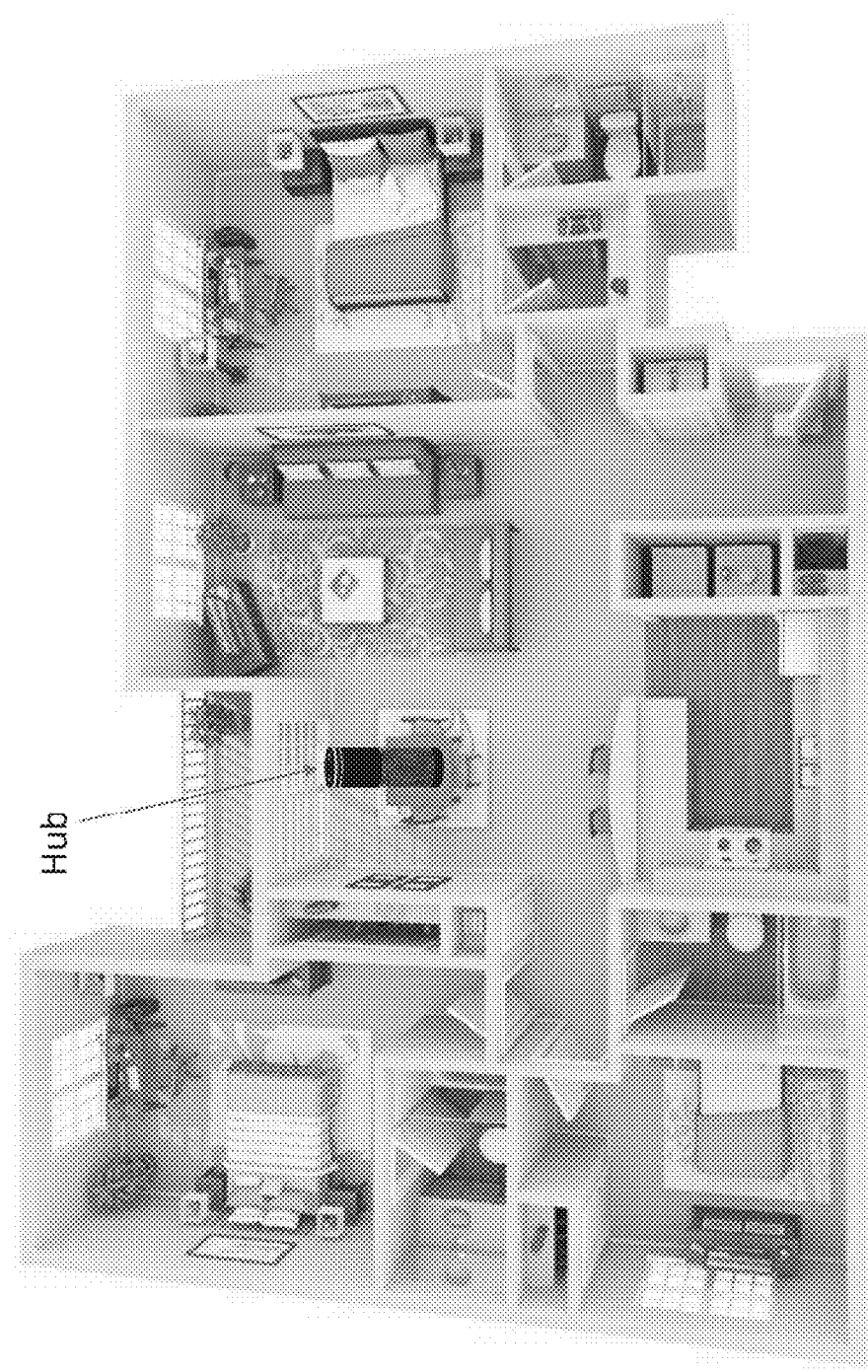
FIG. 6 is a simplified diagram of a hub in a spatial region according to an example of the present invention.

FIG. 6 is a simplified diagram of a hub in a spatial region according to an example of the present invention. This diagram is merely an example, which should not unduly limit the scope of the claims herein. As shown, the hub is deployed in the middle of the living space in a house.

Figure 7:
FIG. 7 is a simplified diagram of a mini node according to an example of the present invention.

FIG. 7 is a simplified diagram of a mini node according to an example of the present invention. This diagram is merely an example, which should not unduly limit the scope of the claims herein. As shown, the system has sensors, which is a subset of sensors in the hub. The sensors are configured to in various spatial locations to improve coverage area and improve accuracy for detection of critical events (e.g., fall, someone calling for help). The sensors also communicate with the hub via Wi-Fi, Bluetooth, ZigBee or UWB, or other technique. Additionally, the sensors or each mini node is deployed in a bathrooms, where chances of fall is high, a kitchen, where we can learn about eating habits by listening to sounds, RF waves, vibrations, or a perimeter of the living space, that will allow us to learn approximate map of the space under consideration, among other locations. Additionally, each of the mini modes can save power and costs by adding more complexity on the hub. This can even enable us to operate on battery for extended periods. For example, each of the nodes can have only single antenna Wi-Fi and hub could have multiple antennas, for WiFi based sensing. Additionally, each of the nodes use simpler radar (e.g., single antenna doppler) vs MIMO FMCW in the HUB. Additionally, each node can be configured with a single microphone whereas the hub can have array of microphone. Of course, there can be other variations, modifications, and alternatives.

Figure 8:
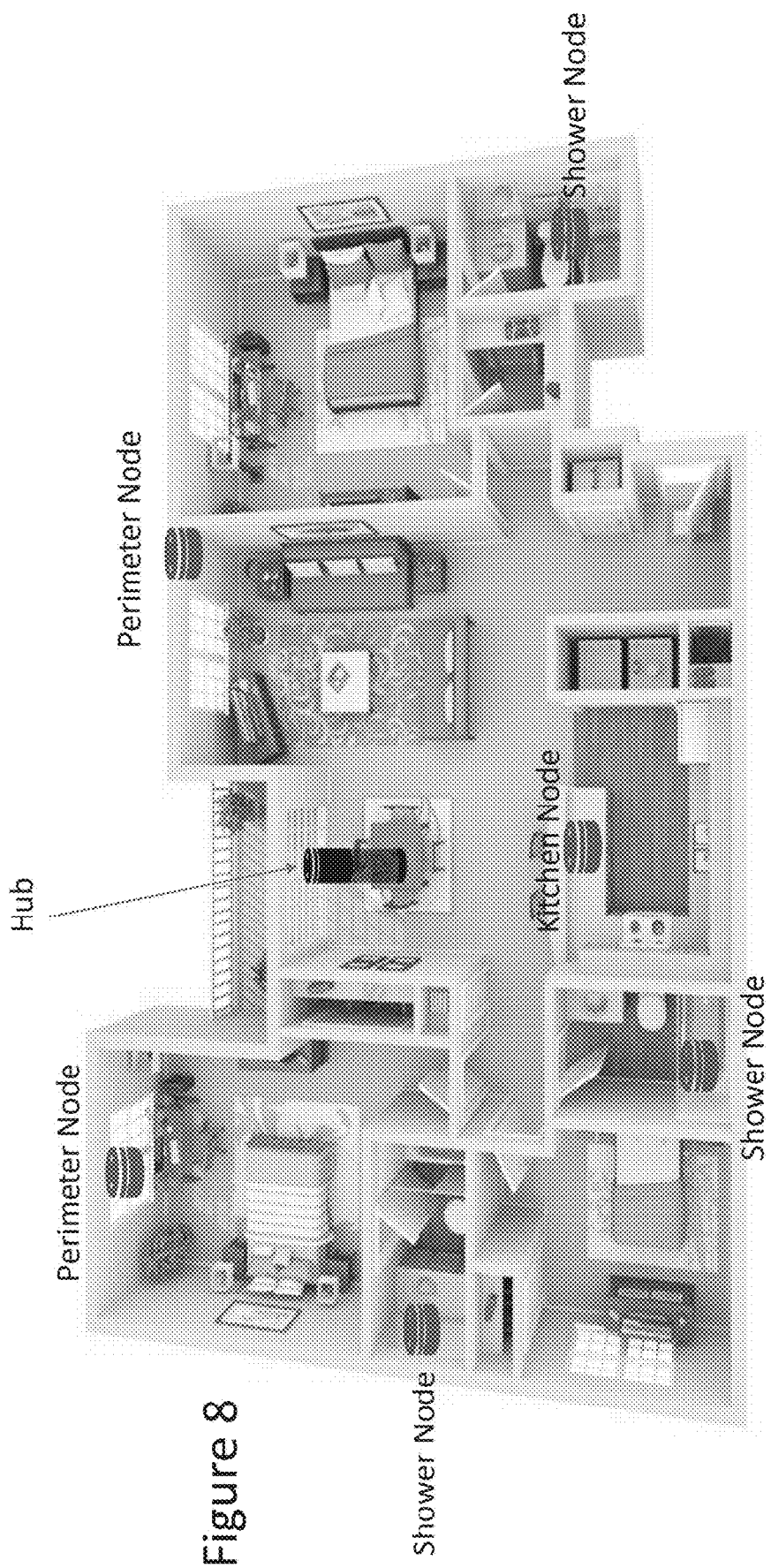
FIG. 8 is a simplified diagram of a mini mode in a spatial region according to an example of the present invention.

FIG. 8 is a simplified diagram of a mini mode in a spatial region according to an example of the present invention. This diagram is merely an example, which should not unduly limit the scope of the claims herein. As shown, each node is configured in a kitchen, shower, perimeter, or other location.

Figure 9:
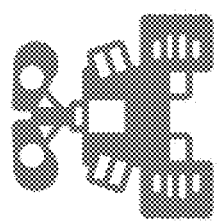
FIG. 9 is a simplified diagram of a mobile node according to an example of the present invention.

FIG. 9 is a simplified diagram of a mobile node according to an example of the present invention. This diagram is merely an example, which should not unduly limit the scope of the claims herein. In an example, each mobile node is a subset of sensors in the hub. The mobile node sensors include a camera such as RGB or IR. In an example, each of the nodes and hub collaboratively figure out interesting events, and pass that information to the mobile node. The technique then goes to the location and probes further. In an example, the camera can be useful to visually find what is going on in the location. In an example, freewill patrolling can be use to detect anything unusual or to refine details of the map created based on perimeter nodes. In an example, onboard UWB can enable precise localization of the mobile node, which can also enable wireless tomography, where the precise RGB and wireless map of the living space is determined.

Figure 10:
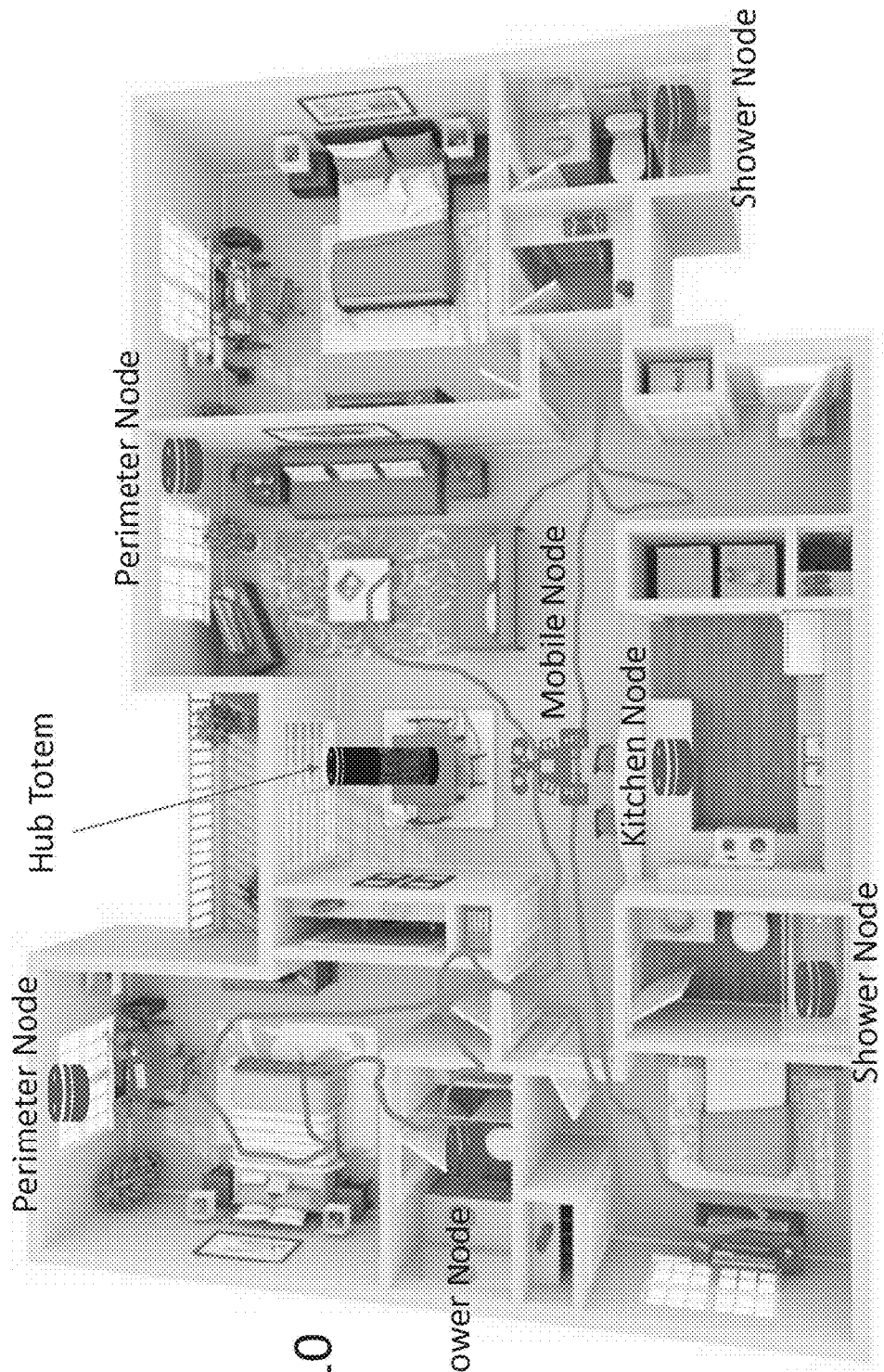
FIG. 10 is a simplified diagram of a mobile mode in a spatial region according to an example of the present invention.

FIG. 10 is a simplified diagram of a mobile mode in a spatial region according to an example of the present invention. This diagram is merely an example, which should not unduly limit the scope of the claims herein. As show, the mobile node, such as a mobile phone or smart phone or other movable device, can physically move throughout the spatial location. The mobile node can also be a drone or other device.

In an example, the technique transfers learned information and activity information to third parties. The technique teaches itself to learn high level behavior that are indicative of a person's welfare using artificial intelligence techniques. In an example, the present technique will then generate summary of such activities and send it out to the human's loved ones, caretaker or even emergency response team depending on the urgency of the situation. For example, for regular days, the technique can simply send short summary like "your mom had a routine activity today", or "She was much less active today." In an example, where the human has a care taker visiting few times a week, the technique can send a notification to them, "It seems she struggles more on yesterday", so that the care taker can pay a visit to make sure everything is fine. Alternatively, the technique can be more acute events like fall, shortness of breathing, or others, that needs quick attention. In these scenarios, the technique can notify medical response team to provide immediate help. Of course, there can be other variations, modifications, and alternatives.

FIG. 11 is a simplified diagram illustrating senor ADL categories in an example. As shown, the present technique can categorize a human target with the listed ADLs, among others.

FIG. 12 is a simplified diagram illustrating an activity list according to an example. As shown, the present technique can determine activities of a human target with any one of the activities listed.

In an example, the present technique can also identify a rare event. In an example, the technique identifies when a senior human falls inside a home with no one around. In an example, the technique is robust, without any false negatives. In an example, the technique uses looking at sequence of events that are before to the potential fall and after a potential fall. In an example, the technique combines the contextual information to robustly determine if a fall has occurred. Of course, there can be other variations, modifications, and alternatives.

In an example, the technique also detects and measures vital signs of each human target by continuous, non-intrusive method. In an example, the vital signs of interest include a heart rate and a respiratory rate, which can provide valuable information about the human's wellness. Additionally, the heart rate and respiratory rate can also be used to identify a particular person, if more than two target humans living in a home. Of course, there can be other variations, modifications, and alternatives.

By understanding the context of how the target human (e.g., elderly) is doing, the technique can also provide valuable feedback directly to the elderly using a voice interface. For example, the technique can sense a mood of the human based on sequence of activities and vital signs of the human and then ask, "Hi do you want me to call your son". Based upon the feedback from the human, the technique can help connect to a third party (or loved one) if their answer is positive. Of course, there can be other alternatives, variations, and modifications.

Having described various embodiments, examples, and implementations, it should be apparent to those skilled in the relevant art that the foregoing is illustrative only and not limiting, having been presented by way of example only. Many other schemes for distributing functions among the various functional elements of the illustrated embodiment or example are possible. The functions of any element may be carried out in various ways in alternative embodiments or examples.

Also, the functions of several elements may, in alternative embodiments or examples, be carried out by fewer, or a single, element. Similarly, in some embodiments, any functional element may perform fewer, or different, operations than those described with respect to the illustrated embodiment or example. Also, functional elements shown as distinct for purposes of illustration may be incorporated within other functional elements in a particular implementation. Also, the sequencing of functions or portions of functions generally may be altered. Certain functional elements, files, data structures, and so one may be described in the illustrated embodiments as located in system memory of a particular or hub. In other embodiments, however, they may be located on, or distributed across, systems or other platforms that are co-located and/or remote from each other. For example, any one or more of data files or data structures described as co-located on and "local" to a server or other computer may be located in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures of files may be used and various described data structures of files may be combined or otherwise arranged.

In other examples, combinations or sub-combinations of the above disclosed invention can be advantageously made. Some embodiments may incorporate smart speaker interface and controls, such as currently provided by Google Home, Amazon Alexa, Apple HomePod and others. For example, using the sensor and AI techniques described above, the device may perform appropriate actions. As examples of this, if the device determines that the user has fallen down and cannot get up, the device may call for help, turn on all the lights, and/or unlock the doors; if the device determines that the user is cooking, the device may turn on an exhaust fan, increase sensitivity for a smoke detector, and/or turn on the lights in the kitchen; if the device determines that the user is alone watching television, the device may turn off lights in other rooms; turn down the light in the room the user is in; and turn off music playing in other rooms; and the like. In light of the present disclosure, one of ordinary skill in the art should recognize many other types of actions that may be performed based upon the user sensed activity.

The block diagrams of the architecture and flow charts are grouped for ease of understanding. However it should be understood that combinations of blocks, additions of new blocks, re-arrangement of blocks, and the like are contemplated in alternative embodiments of the present invention. Further examples of embodiments of the present invention are provided in the attached appendix.

Examples of processing techniques can be found in Exhibit 1, which is incorporated by reference herein.

The specification and drawings are, accordingly, to be regarded in an illustrative rather than a restrictive sense. It will, however, be evident that various modifications and changes may be made thereunto without departing from the broader spirit and scope of the invention as set forth in the claims.

The invention claimed is:

1. A system configured for contactless sleep monitoring of an individual and improvement of a sleep of the individual, the system comprising:
   (a) a housing that comprises both of:
      (i) a transmitter that transmits a wireless signal towards the individual; and
      (ii) a receiver that receives a reflected signal comprising at least a portion of the wireless signal that is reflected back from the individual;
   (b) at least one processor; and
   (c) at least one non-transitory computer readable medium that includes software comprising an artificial intelligence algorithm, wherein the software is configured to cause the at least one processor to:
      (i) determine, using the artificial intelligence algorithm, a parameter associated with the sleep of the individual based on the reflected signal; and
      (ii) prescribe an action that when carried out modifies the parameter associated with the sleep of the individual resulting in the improvement of the sleep of the individual or an environmental condition that when changed modifies the parameter associated with the sleep of the individual resulting in the improvement of the sleep of the individual.

2. The system of claim 1, wherein the software causes the at least one processor to determine the parameter associated with the sleep of the individual by using the artificial intelligence algorithm to identify one or more patterns within the reflected signal.

3. The system of claim 2, wherein the software causes the at least one processor to determine the parameter associated with the sleep of the individual by using the artificial intelligence algorithm to correlate the one or more patterns to one or more baseline values for the individual.

4. The system of claim 3, wherein the one or more baseline values are each previously determined sleep parameters for the individual.

5. The system of claim 1, wherein the parameter associated with the sleep of the individual is determined based on a change in the reflected signal.

6. The system of claim 5, wherein the change in the reflected signal is caused by a vibration of at least a portion of a body of the individual and thereby the reflected signal indicates that the vibration has occurred.

7. The system of claim 6, wherein the parameter associated with the sleep of the individual comprises a vital sign that is determined based at least in part on the vibration.

8. The system of claim 1, wherein the parameter associated with the sleep of the individual comprises a movement of the individual.

9. The system of claim 8, wherein the movement comprises tossing and turning of the individual.

10. The system of claim 1, wherein the artificial intelligence algorithm at least in part filters the reflected signal based on previously received reflected signals for the individual.

11. The system of the claim 10, wherein the artificial intelligence algorithm at least in part identifies the reflected signal as having been reflected back from the individual and not another individual or an object.

12. The system of claim 1, further comprising a sensor configured to sense the environmental condition, and wherein the sensor is a thermometer, a photo diode, a UV sensor, a carbon monoxide sensor, a smoke detector, or a pollen sensor.

13. The system of claim 12, wherein the sensor is not disposed in the housing.

14. The system of claim 12, wherein the software is further configured to cause the at least one processor to determine a device setting of a device that reduces an effect of the environmental factor on the sleep of the individual and transmit a command to the device to adjust in accordance with the device setting that is determined.

15. The system of claim 1, further comprising a microphone that receives an audio signal from the individual or from an environment in which the individual is sleeping.

16. The system of claim 15, wherein the software further causes the at least one processor to associate the audio signal with a factor that affects the sleep of the individual.

17. The system of claim 16, wherein the factor is duration of TV watching by the individual.

18. A system configured for contactless sleep monitoring of an individual and improvement of a sleep of the individual, the system comprising:
 (a) a housing that comprises both of:
  (i) a transmitter that transmits a wireless signal towards the individual; and
  (ii) a receiver that receives a reflected signal comprising at least a portion of the wireless signal that is reflected back from the individual;
 (b) at least one processor; and
 (c) at least one non-transitory computer readable medium that includes software, wherein the software is configured to cause the at least one processor to:
  (i) determine a parameter associated with the sleep of the individual based on the reflected signal; and
  (ii) prescribe an action that when carried out modifies the parameter associated with the sleep of the individual resulting in the improvement of the sleep of the individual or an environmental condition that when changed modifies the parameter associated with the sleep of the individual resulting in the improvement of the sleep of the individual.

19. The system of claim 18, wherein the parameter associated with the sleep of the individual comprises a vital sign.

20. The system of claim 18, wherein the parameter associated with the sleep of the individual comprises a movement of the individual.

21. The system of claim 18, further comprising a sensor configured to sense the environmental condition, and wherein the sensor is a thermometer, a photo diode, a UV sensor, a carbon monoxide sensor, a smoke detector, or a pollen sensor.

22. The system of claim 18, wherein the software is further configured to cause the at least one processor to determine a device setting of a device that reduces an effect of the environmental condition on the sleep of the individual and transmit a command to the device to adjust in accordance with the device setting that is determined.

23. The system of claim 18, further comprising a microphone that receives an audio signal from the individual or from an environment in which the individual is sleeping.

24. A system configured for contactless sleep monitoring and improvement of a sleep of an individual, the system comprising:
 (a) a housing that comprises both of:
  (i) a transmitter that transmits a wireless signal towards the individual; and
  (ii) a receiver that receives a reflected signal comprising at least a portion of the wireless signal that is reflected back from the individual;
 (b) at least one processor; and
 (c) at least one non-transitory computer readable medium that includes software, wherein the software is configured to cause the at least one processor to:
  (i) determine a parameter associated with the sleep of the individual based on the reflected signal; and
  (ii) prescribe, based on the parameter associated with the sleep of the individual, an activity that when carried out by the individual results in the improvement of the sleep of the individual, and
 wherein the system provides one or more incentives to the individual to carry out the activity.

25. The system of claim 24, wherein the parameter associated with the sleep of the individual comprises a vital sign.

26. The system of claim 24, wherein the parameter associated with the sleep of the individual comprises a movement of the individual.

* * * * *